United States Patent
Challand et al.

(10) Patent No.: US 10,330,669 B2
(45) Date of Patent: Jun. 25, 2019

(54) 3D ADCC NK FACS ASSAY

(71) Applicant: Hoffmann-La Roche Inc., Little Falls, NJ (US)

(72) Inventors: Andrea Challand, Penzberg (DE); Christian Klein, Bonstetten (CH); Manfred Kubbies, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 235 days.

(21) Appl. No.: 15/148,938

(22) Filed: May 6, 2016

(65) Prior Publication Data

US 2016/0252493 A1    Sep. 1, 2016

Related U.S. Application Data

(63) Continuation of application No. 13/577,309, filed as application No. PCT/EP2011/051633 on Feb. 4, 2011, now abandoned.

(30) Foreign Application Priority Data

Feb. 11, 2010    (EP) .................................... 10153277

(51) Int. Cl.
*G01N 33/50* (2006.01)
*G01N 33/49* (2006.01)

(52) U.S. Cl.
CPC ..... *G01N 33/5014* (2013.01); *G01N 33/4915* (2013.01); *G01N 33/5017* (2013.01); *G01N 33/5044* (2013.01); *G01N 33/5047* (2013.01)

(58) Field of Classification Search
CPC ........... G01N 33/5014; G01N 33/5032; G01N 33/5044; G01N 33/5047; G01N 33/4915; G01N 33/5017
See application file for complete search history.

(56) References Cited

U.S. PATENT DOCUMENTS

| 5,420,016 A | 5/1995 | Boguslaski et al. |
| 2004/0219224 A1 | 11/2004 | Yakovlevsky et al. |

FOREIGN PATENT DOCUMENTS

| JP | A-H1-126558 | 1/1999 | |
| JP | T 2009-522583 | 6/2009 | |
| WO | 2005/009465 A1 | 2/2005 | |
| WO | 2005/044859 A2 | 5/2005 | |
| WO | 2005/044859 A3 | 5/2005 | |
| WO | WO 2007/082138 * | 7/2007 | ......... G01N 33/5044 |
| WO | 2009/041113 A1 | 4/2009 | |
| WO | 2009/-41113 A1 | 4/2009 | |

OTHER PUBLICATIONS

Koichi et al. Antitumor activity of anti-C-ERC/ mesothelin monoclonal antibody in vivo. Cancer Science 101 (4): 969-974 (Jan. 20, 2010).*
Written Opinion of the International Searching Authority for International Patent Application No. PCT/EP2011/051633, (2005).
Deaglio et al., "Human CD38 and CD16 are functionally dependent and physically associated in natural killer cells" Blood 99(7):2490-2498 ( 2002).
Flieger et al., "A novel non-radioactive cellular cytotoxicity test based on the differential assessment of living and killed target and effector cells" J Immunol Meth 180:1-13 ( 1995).
Friedrich et al., "Experimental anti-tumor therapy in 3-D: Spheroids—old hat or new challenge?" Int J Radiat Biol 83:849-471 ( 2007).
Graff et al., "Theoretical Analysis of Antibody Targeting of Tumor Spheroids: Importance of Dosage for Penetration, and Affinity for Retention" Cancer Research 63:1288-1296 (Mar. 15, 2003).
Horgan et al., "Immunomagnetic purification of T cell subpopulations" Current Protocols in Immunol( Suppl 85):7.4.1-4.4.9 (Apr. 2009).
Inami et al., "Antitumor activity of anti-C-ERC/mesothelin monoclonal antibody in vivo" Cancer Sci 101:969-974 ( 2010).
Ivascu and Kubbies, "Rapid generation of single-tumor spheroids for high-throughput cell function and toxicity analysis" J Biomol Screening 11:922-932 ( 2006).
Iwasaki et al., "Infiltrative and Cytolytic Activities of Lymphokine-activated Killer Cells against a Human Glioma Spheroid Model" Cancer Research 50:2429-2436 (Apr. 15, 1990).
Jääskeläinen et al., "Effect of LAK Cells Against Three-Dimensional Tumor Tissue In Vitro Study Using Multi-Cellular Human Glioma Spheroids as Targets" The Journal of Immunology 142(3):1306-1045 (Feb. 1, 1989).
Kelm et al., "Method for generation of homogeneous multicellular tumor spheroids applicable to a wide variety of cell types" Biotecnol Bioeng 83:173-180 ( 2003).
Liu et al., "Apoptosis of Raji cells by an anti-CD20 antibody HI47 and its fragments" Leukemia Res 28:209-211 ( 2004).
Masuda et al., "Enhanced binding affinity for FcγRIIIa of fucose-negative antibody is sufficient to induce maximal antibody-dependent cellular cytotoxicity" Molec Immunol 44:3122-3131 (May 2007).
Moscona, A., "Rotation-mediated histogenetic aggregation of dissociated cells" Exp Cell Res 22:455-475 ( 1961).
Mueller-Klieser, W., "Tumor biology and experimental therapeutics" Crit Rev Oncol Hematol 36:123-139 ( 2000).
Neurauter et al., "Cell isolation and expansion using Dynabeads" Adv Biochem Eng Biotechnol (Abstract only), 106:41-73 ( 2007).

(Continued)

*Primary Examiner* — Gailene Gabel
(74) *Attorney, Agent, or Firm* — Jonathan Aumais (57) ABSTRACT

Herein is reported a cell analytical technology based on a three-dimensional spheroid/aggregate co-culture assay, wherein the spheroid or aggregate is formed of tumor and natural killer cells. This method is useful for the in vitro functional analysis of antibodies in single and high-throughput format.

8 Claims, 7 Drawing Sheets

(56) References Cited

OTHER PUBLICATIONS

Ong et al., "Engineering a scaffold-free 3D tumor model for in vitro drug penetration studies" Biomaterials 31:1180-1190 (2010).
Ortaldo et al., "Analysis of effector cells in human antibody-dependent cellular cytotoxicity with murine mnoclonal antibbodies" J Immunol 138(10):3566-3572 (May 15, 1987).
Sutherland and Durand, Recent Results Cancer Res 95:24-49 (1984).

\* cited by examiner

Fig. 7 no antibody      anti-CD20 antibody

3D ADCC NK FACS ASSAY

CROSS REFERENCE TO RELATED APPLICATIONS

This application is a continuation of U.S. patent application Ser. No. 13/577,309 filed Aug. 6, 2012, now abandoned, which is a National Stage application of PCT/EP2011/051633, filed Feb. 4, 2011, which claims priority to European Patent Application No. 10153277.8, filed Feb. 11, 2010, the disclosure of which are incorporated hereby reference in their entirety.

Herein is reported a novel antibody-dependent-cytotoxicity-FACS-assay based on a three-dimensional spheroid or an aggregate formed of lymphoma cells and natural killer cells. This assay is useful for the in vitro functional analysis of therapeutic immunoglobulins in single as well as high-throughput format.

BACKGROUND OF THE INVENTION

Monolayer cultures of established tumor cell lines are frequently used in basic tumor biology research and antitumor drug development. However, a two-dimensional, flat culture model insufficiently reflects the three-dimensional (3D) tumor architecture. Therefore, specific aspects related to the in vivo development of solute diffusion gradients can only be studied in a three-dimensional culture system like for instance the multicellular tumor spheroid or aggregate model. Tumor spheroids or aggregates mimic avascular tumor regions, characterized by limited nutrient supply due to diffusion barriers through multicellular layers.

However, the widespread use of 3D cultures in research is limited by inconvenient generation and handling. Therefore, a simple and rapid method was developed to generate single spheroids or aggregates in suspension culture in a high-throughput fashion. Single spheroids or aggregates with equal sizes and homogenous spherical geometry can be generated in single wells of a 96-well plate within a 24 hour culture period. It is a standardized culture format with easy access for compound handling and spheroid harvest for subsequent analysis. The uniform size and geometry guarantees the development of almost identical diffusion gradients in each spheroid or aggregate (Ivascu, A. and Kubbies, M., J. Biomol. Screening 11 (2006) 922-932). The known spheroid generation protocol includes the addition of a murine basement membrane extract (rBM), a mixture of extracellular matrix proteins that induces a compaction of the aggregate to a spheroid.

Inami, K., et al. report antitumor activity of anti-C-ERC/mesothelin monoclonal antibody in vivo (Cancer Sci. 101 (2010) 969-974).

SUMMARY OF THE INVENTION

It has been found that with the combination of tumor cells and natural killer cells in a three-dimensional spheroid or aggregate the evaluation of immunoglobulins can on the one hand be made more in vivo like and on the other hand is now suited for high-throughput analysis.

A first aspect as reported herein is a method for in vitro detection of the effector function of an antibody comprising the step of incubating a three-dimensional spheroid or aggregate comprising tumor cells and natural killer cells with the immunoglobulin.

In one embodiment the method comprises the following steps:

a) labeling tumor target cells with a first fluorescent dye,
b) mixing natural killer cells and tumor target cells,
c) adding about $10^4$ cells per 200 µl to a well of a multi well plate,
d) centrifuging the multi-well plate and thereby initiating the forming of a three-dimensional cell spheroid,
e) adding the immunoglobulin to the wells of the multi well plate,
f) incubating the multi-well plate for about 20 hours to about 72 hours,
g) labeling dead cells in the wells with a second fluorescent dye, and
i) analyzing the cells in the wells of the multi well plate by fluorescence activated cell sorting (FACS) and thereby detecting the effector function of the antibody.

In one embodiment the natural killer cells are human natural killer cells and have a purity of 90% or more. In a further embodiment the natural killer cells and tumor target cells are mixed at a ratio of from 10:1 to 1:10. In a further embodiment the ratio is of from 1:3 to 1:10. In another embodiment the ratio is of from 1:2 to 1:4. In one embodiment the centrifuging is for 10 min. at 100 to 1,000 rpm. In a further embodiment the centrifuging is at about 1,000 rpm. In one embodiment the second fluorescent dye is propidium iodide. In one embodiment the incubating is for about 20 hours to about 28 hours.

In one embodiment the tumor cells are lymphoma cells. In another embodiment the lymphoma cell is selected from the group comprising Raji-cells, SU-DHL4 cells, and Z138 cells. In another embodiment the antibody is added at a final concentration in the well of from 100 µg/ml to 0.001 µg/ml. In a further embodiment the antibody is added at a final concentration in the well of from 20 µg/ml to 0.1 µg/ml. In one embodiment the antibody is added at a final concentration in the well of from 8 µg/ml to 12 µg/ml.

A further aspect as reported herein is the use of a three-dimensional spheroid or aggregate comprising tumor cells and natural killer cells for the high-throughput analysis of the combination of a multitude of antibodies and a multitude of tumor cells.

Another aspect as reported herein is a method for determining in vitro an antibody with effector function comprising a) providing at least one antibody,
b) labeling tumor cells with a first fluorescent dye,
c) mixing natural killer cells and tumor target cells,
d) adding about $10^4$ cells per 200 µl to the wells of a multi well plate,
e) centrifuging the multi-well plate and thereby initiating the forming of a three-dimensional cell spheroid,
f) adding each of the provided antibodies to an individual well of the multi well plate,
g) incubating the multi-well plate for about 20 hours to about 72 hours
h) labeling dead cells in each of the incubated wells with a second fluorescent dye,
i) analyzing each well of the multi well plate by fluorescence activated cell sorting, and
j) determining the antibody with the highest ratio or a ratio of more than 1 of dead cells to viable cells as antibody with effector function.

Also an aspect as reported herein is a kit comprising:
a) a tumor cell labeled with a fluorescent dye,
b) isolated natural killer cells,
c) a 96-well multi well plate, and
d) propidium iodide.

In one embodiment the multi well plate is a 96-well multi well plate.

DETAILED DESCRIPTION OF THE INVENTION

Herein is reported a cell analytical technology based on the use of a three-dimensional spheroid or aggregate co-culture assay, wherein the spheroids or aggregates comprise tumor cells and natural killer cells. This assay is useful in one embodiment for the in vitro functional analysis of immunoglobulins in single and high-throughput format. In one embodiment a single three-dimensional spheroid or aggregate is placed in each well of a 96-well round bottom multi well plate that has been coated with polyHEMA (poly (hydroxyethyl methacrylic) acid). In a further embodiment the NK cells are normal diploid human natural killer (NK) cells. In one embodiment the NK cells have been selected by applying a negative selection technique, i.e. the cells are not touched during the selection step (see e.g. Horgan, K. et al., Curr. Prot. Immunol. (2009), Chapter 7, Unit 7.4. Immunomagnetic purification of T cell subpopulations, and Neurauter, A. A., et al., Adv. Biochem. Eng. Biotechnol. 106 (2007) 41-73). It has been found that it is possible with these NK cells to quantitate correct percentages of viable and dead cells.

Most of the in vitro experiments in the field of tumor biology are performed with monolayer cultures since these are easy and convenient to handle. However, although they provide a valuable model to study distinct functions, monolayer cultures insufficiently reflect the tumor pathobiology due to the lack of stroma components, extracellular matrix and fundamental geometric differences between two-dimensional (2D) cultures and three-dimensional (3D) solid tumors. The three-dimensional organization of cells provides a complex network of cell-cell and cell-matrix interactions relevant e.g. for distribution and function of hormones, growth factors and nutrients influencing cellular differentiation, proliferation and survival.

In one embodiment the method for the generation of three dimensional spheroids from aggregates comprises the addition of reconstituted basement matrix derived from the Engelbreth-Holm-Swarm murine tumor (rBM, Matrigel™), a proteinaceous gel containing extracellular matrix components such as collagens, laminin, fibronectin, entactin (nidogen), and proteoglycans, to the cultivation medium. The three-dimensional architecture allows the co-cultivation of tumor cells with fibroblast, immune and endothelial cells, enabling the investigation of tumor/stroma interaction effects in vitro (Friedrich, J., et al., Int. J. Radiat. Biol. 83 (2007) 849-871).

In the spinner (Sutherland, R. M. and Durand, R. E., Recent Results Cancer Res. 95 (1984) 24-49) and the gyratory rotation technique (Moscona, A., Exp. Cell Res. 22 (1961) 455-475) trypsinized cells are placed in a culture vessel with a magnetic stirrer inhibiting cell attachment to the substrate and favoring cell-cell adhesion. In a more recently developed technique, spheroids are grown in a hanging drop of an inverted microplate (Kelm, J. M., et al., Biotechnol. Bioeng. 83 (2003) 173-180). However, all these methods are limited by either long cultivation time, formation of unequal-size spheroids, or difficult mechanical accessibility. In addition, in suspension cultures, many tumor cell lines grow poorly in three dimensional compact spheroids (Mueller-Klieser, W., Crit. Rev. Oncol. Hematol. 36 (2000) 123-139).

The use of spheroids or aggregates in a high-throughput fashion in research requires a standardized protocol that rapidly generates spheroids of homogenous size with similar diffusion gradients and cell physiology in a multi-well plate format that is easily accessible for subsequent biochemical or cell analysis. Moreover such a protocol should be applicable to a large variety of tumor cell lines.

It has been found that this need can be fulfilled with the methods as reported herein. Therefore, one aspect as reported herein is an assay for detection of effector function of an antibody comprising
a) labeling lymphoma (target) cells with the green fluorophore CMFDA (5-chloromethylfluorescein diacetate),
b) isolating human normal natural killer (NK) cells from human blood, in one embodiment with a purity of more than 90%,
c) mixing NK and lymphoma target cells at a ratio of from 1:10 to 10:1,
d) adding about $10^4$ cells per 200 μl to some or all of the wells of a multi well plate,
e) centrifuging the multi-well plate,
f) adding the immunoglobulin of interest to the wells of the multi well plate,
g) incubating the multi-well plate for up to 72 h, in one embodiment for 20 h to 72 h,
h) adding propidium iodide to the wells, and
i) analyzing the cells in the wells of the multi well plate by FACS.

It has been found that by the combination of lymphoma cells and natural killer cells a sensitive antibody-dependent-cellular-cytotoxicity assay can be provided. In one embodiment the detection of effector function of an antibody is a detection or determination of antibody-dependent-cellular-cytotoxicity of an antibody. Additionally a three-dimensional assay set-up of tumor and immuno effector function cells is also advantageous. In one embodiment the methods as reported herein are in vitro methods. In another embodiment the mixing of the tumor cells and the natural killer cells results in the formation of a three-dimensional spheroid.

Figure 1:
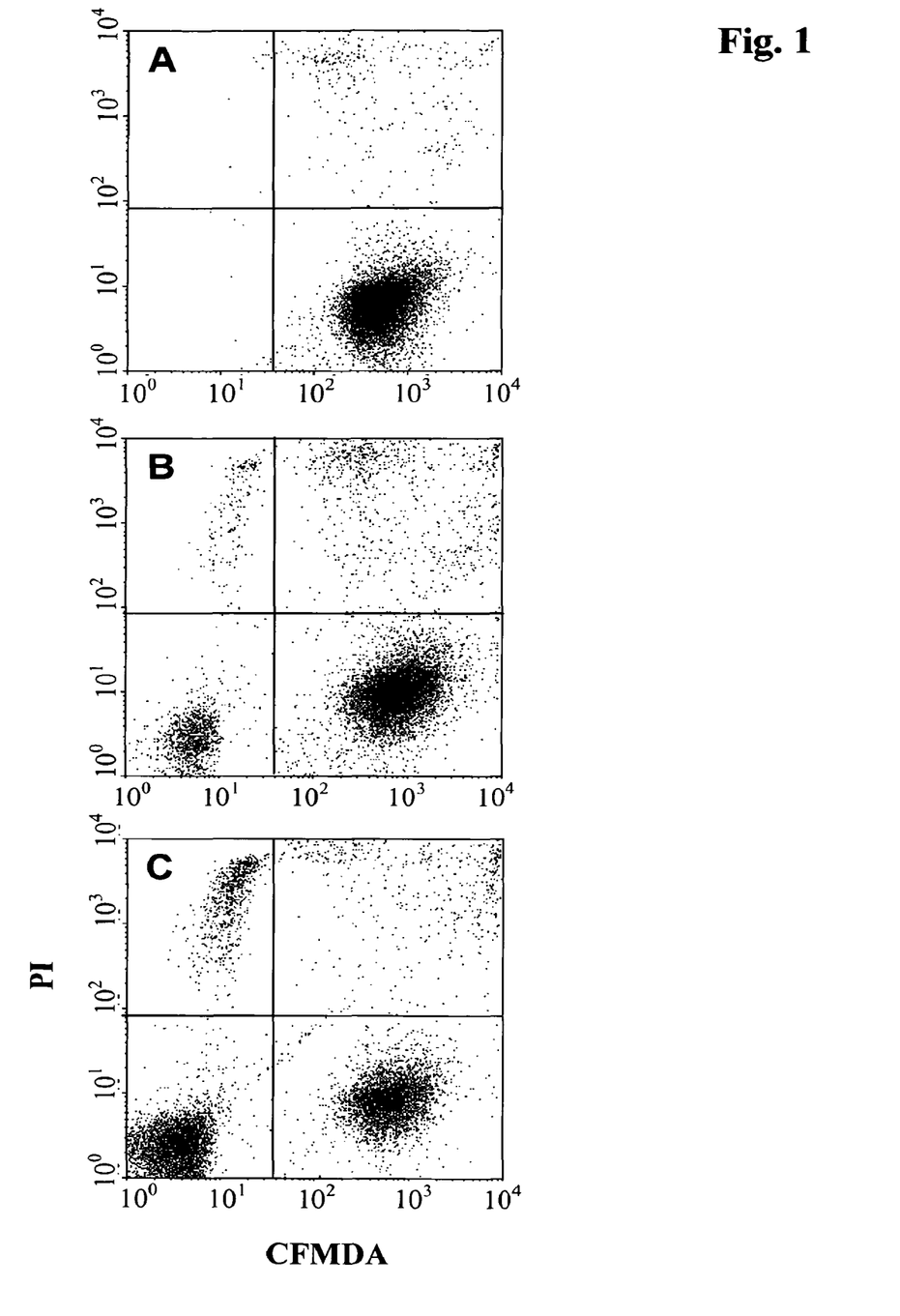
FIG. 1A-C FACS analysis of viable and dead Raji-cells and natural killer (NK) cells in the absence of an antibody. Quadrants: lower left: viable NK cells, upper left: dead NK cells, lower right: viable Raji-cells, upper right: dead Raji-cells.
Figure 2:
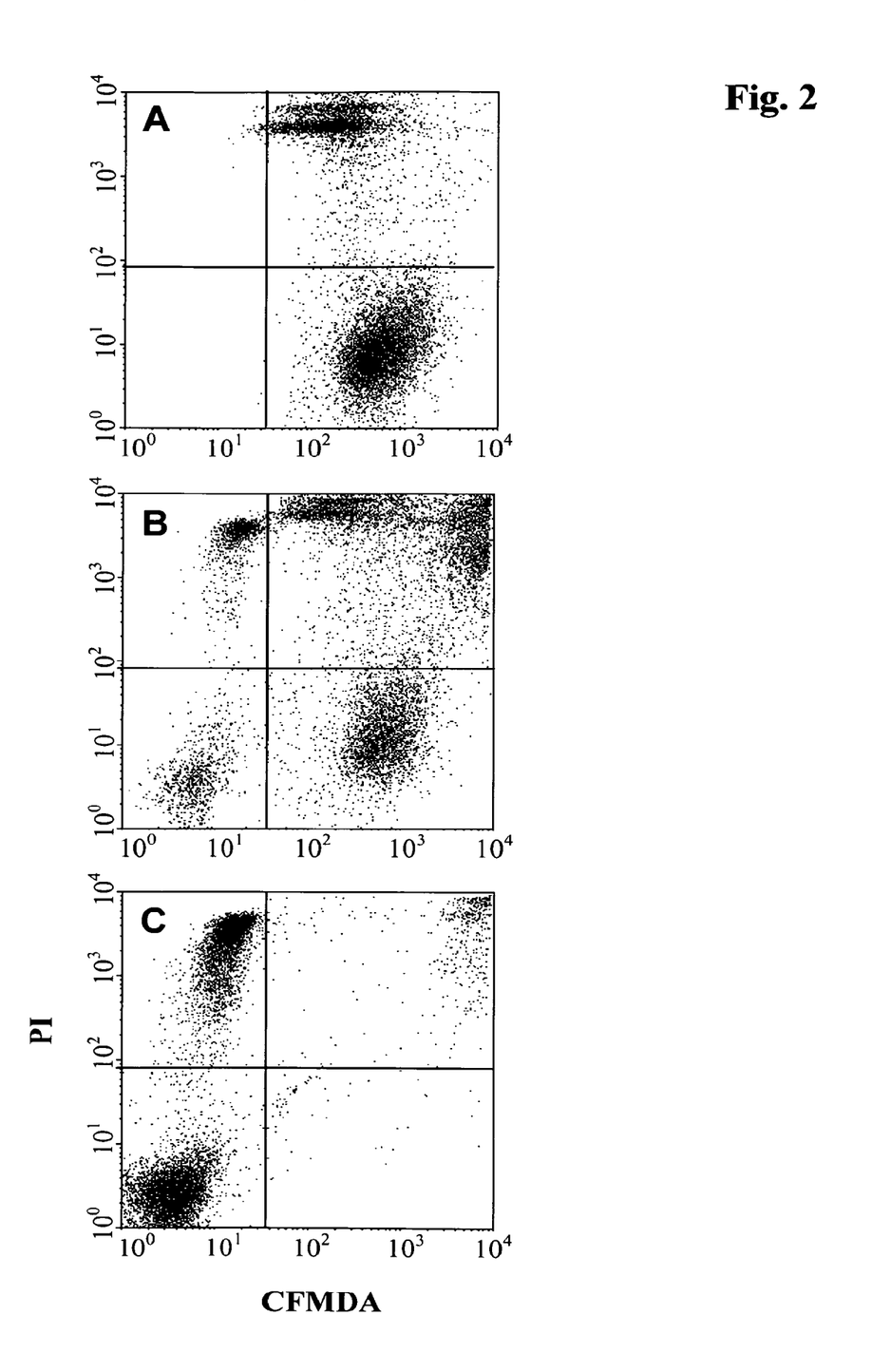
FIG. 2A-C FACS analysis of viable and dead Raji-cells and natural killer cells in the presence of an added anti-CD20 antibody (10 µg/ml). Quadrants: lower left: viable NK cells, upper left: dead NK cells, lower right: viable Raji-cells, upper right: dead Raji-cells.

In FIGS. 1 and 2 the distribution of viable and dead cells analyzed by FACS is shown. FIG. 1a shows the distribution of viable and dead Raji-cells labeled with CMFDA determined by FACS analysis. Viable Raji-cells are located in the lower right sector of the FACS diagram. FIGS. 1b and 1c show the distribution of viable and dead cells of a co-culture of Raji-cells and natural killer cells in the absence of an added antibody. Viable natural killer cells are located in the lower left sector of the FACS diagram, viable Raji-cells are located in the lower right sector of the FACS diagram, dead natural killer cells are located in the upper left sector of the FACS diagram and dead Raji-cells are located in the upper right sector of the FACS diagram. From FIGS. 1b (ratio of Raji to NK cells of 1:1) and 1c (ratio of Raji to NK cells of 1:10) it can be seen that in the absence of antibody and independent of the ratio of Raji-cells to natural killer cells the percentage of the respective viable and dead lymphoma cells is not changed significantly.

FIG. 2a shows the FACS analysis of viable and dead Raji-cells after incubation with an antibody. In comparison with the FACS diagram of FIG. 1a it can be seen that by incubating the Raji-cells with the antibody only, the fraction of dead cells increases due to the direct cell death inducing function of the antibody. In the presence of NK cells the number of dead Raji cells increases even more due to the ADCC effector function (upper right clusters: FIG. 2b Raji/NK ratio 1:1 and FIG. 2c Raji/NK ratio 1:10). It can be seen that by the addition of natural killer cells the sensitivity of the assay can be increased.

In the assay the multi well plates are centrifuged in one embodiment for 10 min. at 1,000 g. During centrifugation all cells within each well are pelleted at the bottom of the well. This ensures equal cell numbers for initiation of the formation of a single spheroid or aggregate in each well.

Figure 3:
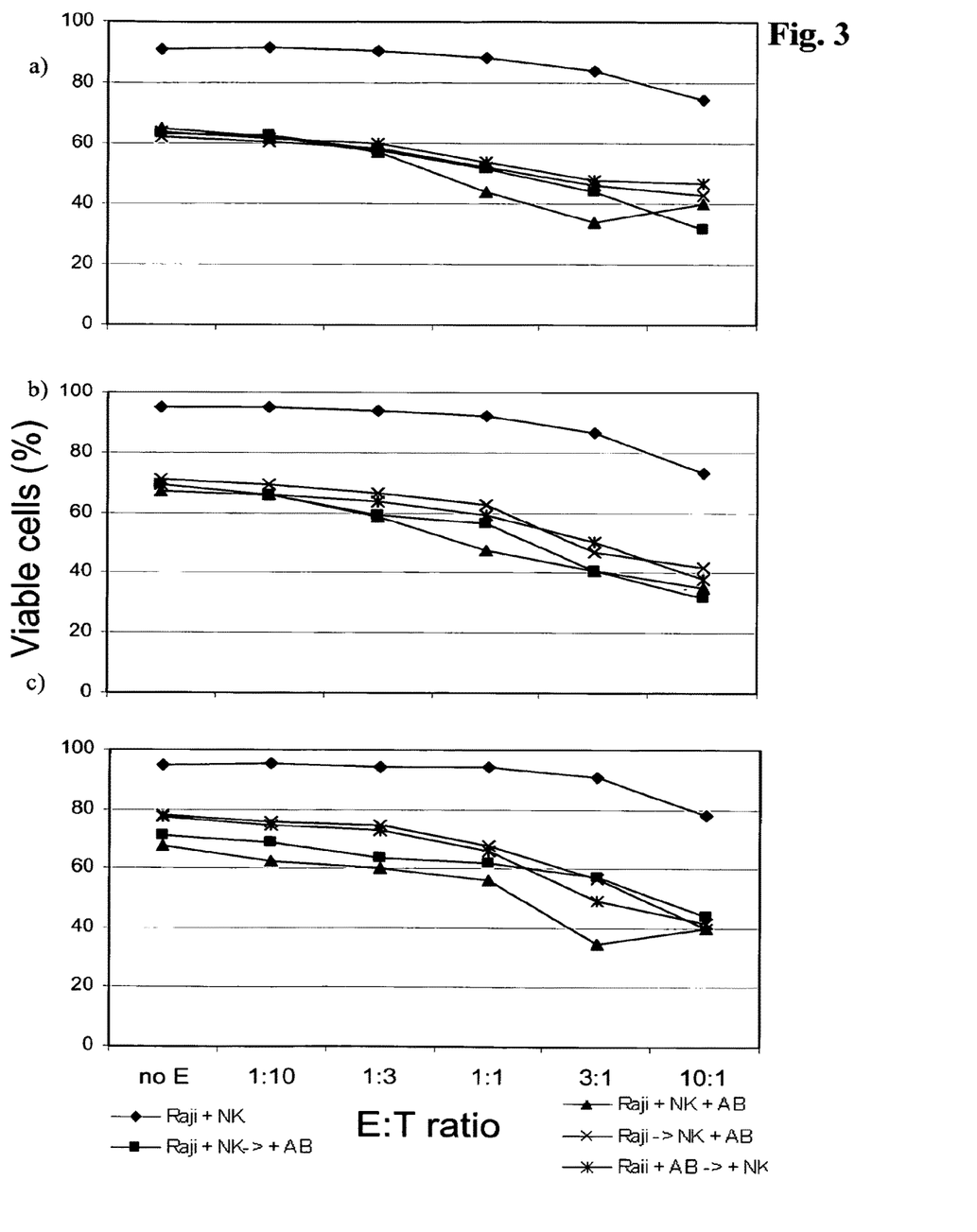
FIG. 3 Optimization of lymphoma/spheroid-aggregate co-culture by variation of lymphoma cell, NK cell and antibody application schedule. Lymphoma cells: Raji-cells.

In FIG. 3 the effect of the sequence of the addition of the individual components, i.e. Raji-cells, natural killer cells and antibody, on the assay is shown. It can be seen that the addition of all three components in parallel gave rise to slightly, but not significantly, higher cell death rates. However, to mimic more closely the in vivo situation, in one embodiment the assay comprises the formation of the lymphoma-NK three-dimensional spheroid or aggregates prior to the addition of the antibody to be tested.

The assay as reported herein can be performed with any tumor (target) cell. In one embodiment the tumor cell is a lymphoma cell. In a further embodiment the lymphoma cell is selected from Raji-cell, SU-DHL4 cell, and Z138 cell.

In one embodiment when using adherently growing carcinoma or sarcoma tumor cells as tumor cells the formation of the three-dimensional spheroid is performed in the presence of liquid reconstituted basement membrane (rBM). In one embodiment a concentration of 2.5% rBM (v/v) is used. In this embodiment all cells were incorporated in one distinct spheroid with a round geometry. Formation and compaction was completed after 24 hours of culture time. Therefore, in one embodiment the incubation is for 20 hours to 28 hours. Lower concentrations of rBM did not ensure the incorporation of all cells into the spheroid, and higher concentrations impaired the round geometry of the spheroids. After the 10 min. centrifugation step, all cells within a well are incorporated into one flat pellet.

Three hours later, some degree of compaction becomes evident in the presence and absence of rBM. Without rBM, no further tightening of the aggregates can be observed after 6 hours and 24 hours. In one embodiment the tumor cell is a Raji-cell and rBM is absent in all steps of the method.

In one embodiment five thousand cells were centrifuged in RPMI 1640 with 10% FCS (fetal calf serum) and 2.5% rBM (v/v). The spheroid size was analyzed after a 24 hour culture period. All spheroids are regular in shape, display a uniform round geometry, and exhibit a narrow size variation.

Figure 4:
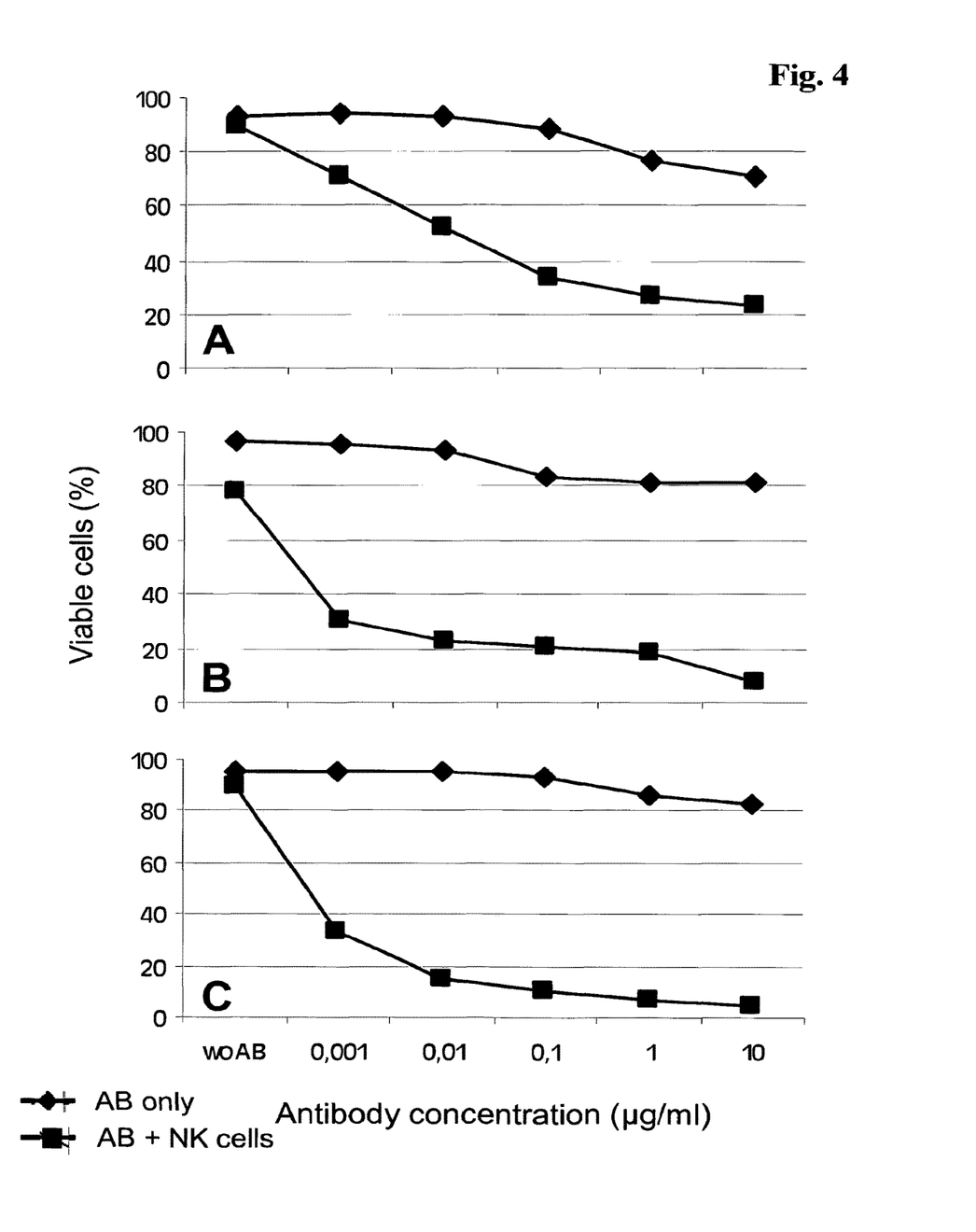

In FIG. 4 the assay as reported herein is performed with different lymphoma tumor (target) cell lines and with different antibody concentrations. It can be seen that the assay as reported herein can be performed with different lymphoma cell lines at the same efficiency. It can further be seen that the assay can be performed at an antibody concentration of from 10 µg/ml to 0.1 µg/ml. Therefore, in one embodiment the assay as reported herein comprises adding the antibody at a concentration of from 0.1 µg/ml to 15 µg/ml, in a further embodiment of from 8 µg/ml to 12 µg/ml.

Figure 5:
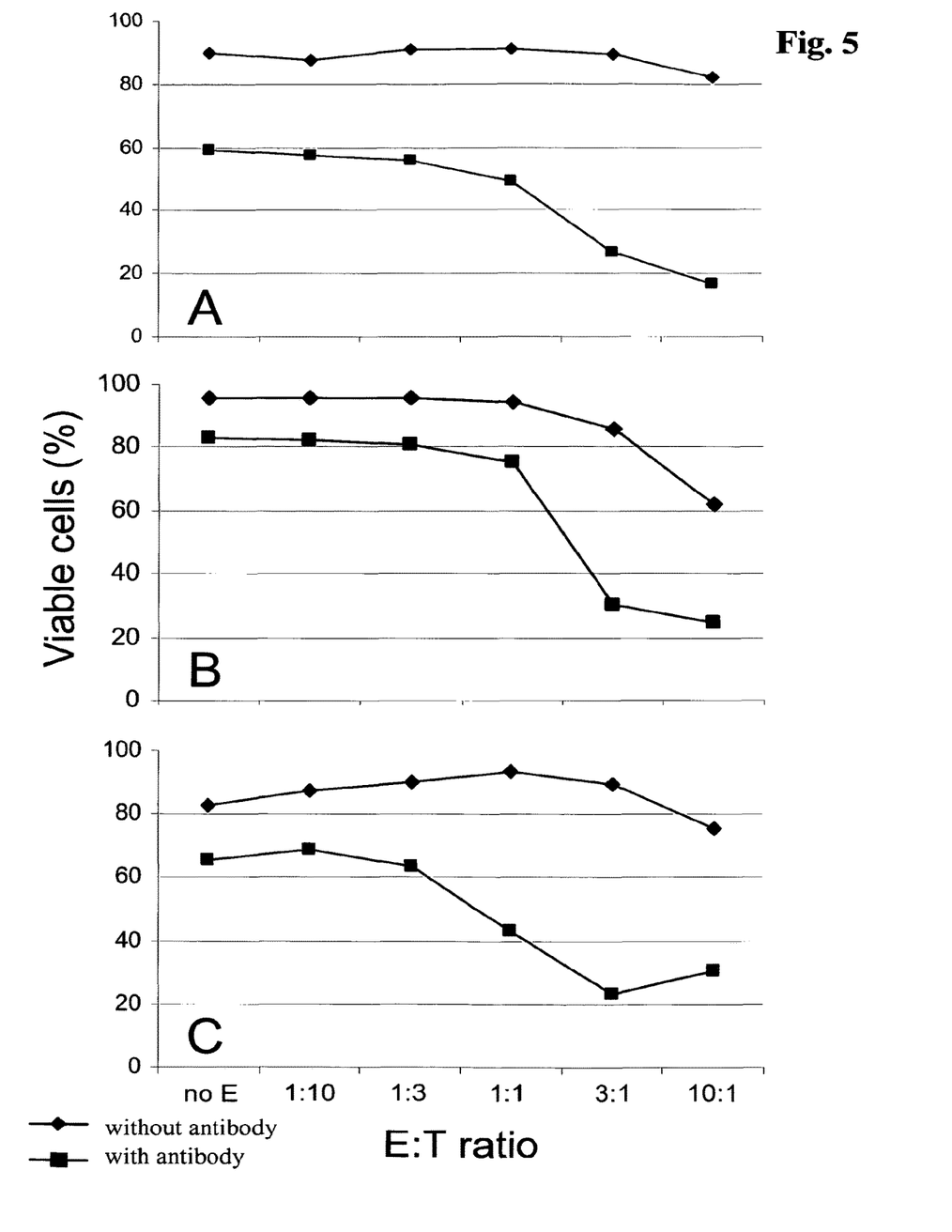
FIG. 5A-C Percentages of viable lymphoma cells in the presence of the anti-CD20 antibody concentration as a function of the effector (NK):target (lymphoma) ratio.

In FIG. 5 the sensitivity of the assay as reported herein depending on the ratio of lymphoma cells to natural killer cells is shown. It can be seen that a ratio of from 1:1 to 1:10 of lymphoma (target) cells to natural killer cells indicates the ADCC effector function of NK cells. Therefore, in one embodiment the ratio of lymphoma cell to natural killer cell is of from 1:1 to 1:10, in another embodiment of from 1:3 to 1:10, in a further embodiment of from 1:2 to 1:4.

With the assay as reported herein single three-dimensional spheroids or aggregates with a narrow size distribution and homogenous spherical geometry can be generated in a single well or in multiple wells of a multi-well plate in parallel within a 24 hour culture period. It has been shown that this can be a standardized culture format with easy access for compound handling and spheroid harvest for subsequent analysis. The almost uniform size and geometry of the spheroids or aggregates guarantees the development of similar diffusion gradients in each spheroid. Therefore, one aspect as reported herein is an automated or high-throughput assay comprising the assay as outlined above. The spheroid generation protocol includes the addition of a murine basement membrane extract (rBM), a mixture of extracellular matrix proteins that induces a compaction of the aggregate to a spheroid.

Figure 6:
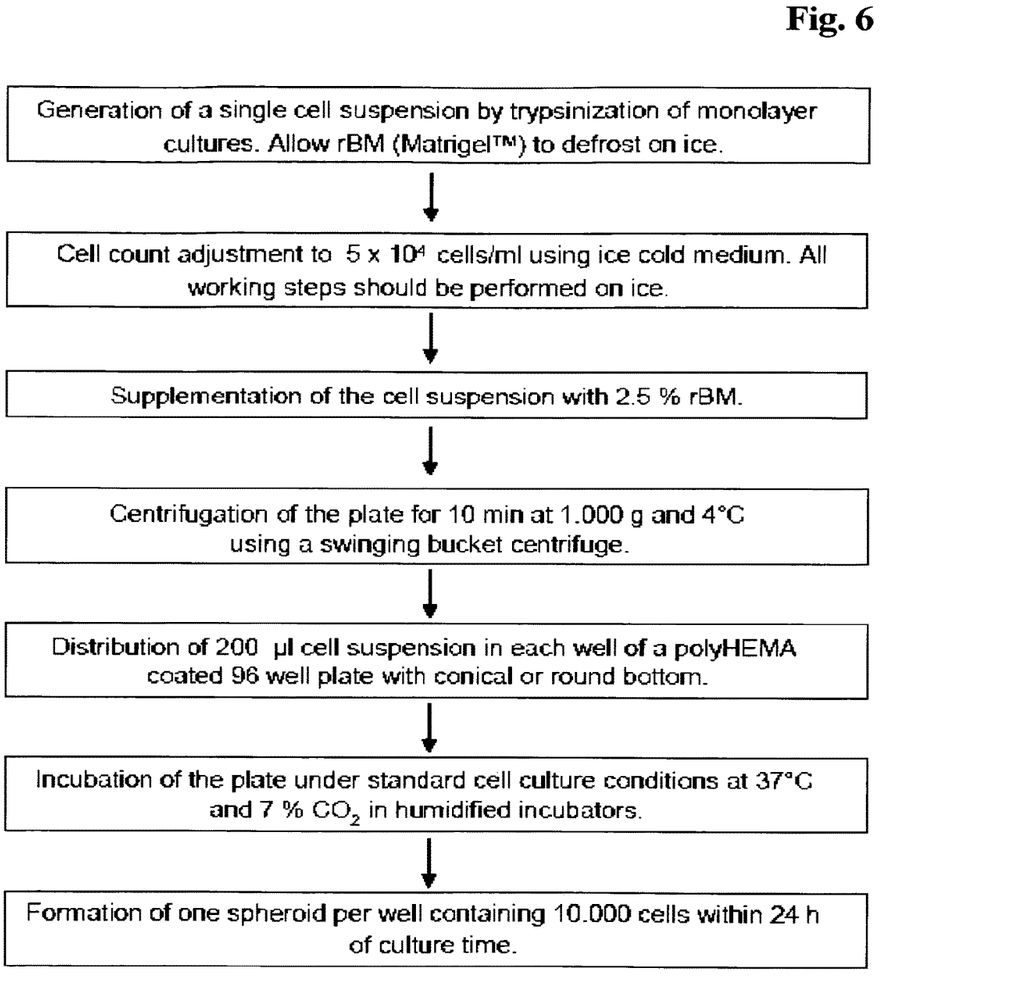
FIG. 6 Schematic exemplary method.

In FIG. 6 an exemplary scheme for the generation of three-dimensional spheroids is shown.

Herein is reported a method for the in vitro detection of effector function of an antibody comprising the incubating of a three-dimensional spheroid or aggregate comprising tumor cells and natural killer cells with the antibody.

In one embodiment the method comprising the following steps:
  mixing natural killer cells and tumor cells,
  adding about $10^4$ cells per 200 µl to the wells of a multi well plate,
  centrifuging the multi-well plate and thereby inducing the formation of a three-dimensional spheroid or aggregate,
  adding the immunoglobulin to the wells of the multi well plate,
  incubating the multi-well plate for about 20 hours to about 72 hours, and
  analyzing the cells in the wells of the multi well plate by fluorescence activated cell sorting and thereby detecting the effector function of the antibody.

In a further embodiment the method comprises in addition the following step as first step:
  labeling tumor cells with a first fluorescent dye.

In another embodiment the method comprises the further steps:
  labeling dead cells with a second fluorescent dye, and
  analyzing the cells in the wells of the multi well plate by fluorescence activated cell sorting and thereby detecting the effector function of the antibody.

In one embodiment the natural killer cells are human natural killer cells. In also an embodiment the natural killer cells and tumor cells are mixed at a ratio of from 10:1 to 1:10. In a further embodiment the ratio is of from 1:2 to 1:4.

In one embodiment the incubating is for about 20 hours to about 28 hours.

In one embodiment the centrifuging is at 1,000 rpm for 10 min.

In one embodiment the tumor cell is a lymphoma cell. In a further embodiment the lymphoma cell is a Raji-cell, or a SU-DHL4 cell, or a Z138 cell.

In one embodiment the antibody is added at a concentration of from 15 µg/ml to 0.1 µg/ml. In another embodiment the antibody is added at a concentration of from 8 µg/ml to 12 µg/ml.

Another aspect as reported herein is the use of a three-dimensional spheroid or aggregate comprising tumor cells and natural killer cells for the determination of effector function of a combination of a multitude of antibodies with a multitude of tumor cells.

A further aspect as reported herein is a method for determining in vitro an antibody with effector function comprising the steps:
  mixing natural killer cells and the tumor cells,
  adding about $10^4$ cells per 200 µl to the wells of a multi well plate, centrifuging the multi-well plate and thereby inducing the formation of a three-dimensional spheroid or aggregate, adding the antibody to an individual well of the multi well plate, incubating the multi-well plate for about 20 hours to about 72 hours, and determining the antibody with a ratio of dead to viable cells as antibody with effector function.

In one embodiment the method comprises in addition the following first steps:

providing at least one antibody, and labeling tumor cells with a first fluorescent dye.

In another embodiment the method comprises the steps:

adding each of the provided antibodies to an individual well of the multi well plate, whereby to each well at most one antibody is added, labeling dead cells in each of the incubated wells with a second fluorescent dye, analyzing the cells in each well of the multi well plate by fluorescence activated cell sorting, and determining the antibody with the highest ratio of dead to viable cells as antibody with effector function.

The assay and method as reported herein is exemplified with an anti-CD20 antibody as reported in WO 2005/044859 (incorporated by reference herein). This antibody has been chosen only for exemplifying the current invention and should not be interpreted as restriction. The scope of the invention is set forth in the claims.

The following examples and figures are provided to aid the understanding of the present invention, the true scope of which is set forth in the appended claims. It is understood that modifications can be made in the procedures set forth without departing from the spirit of the invention.

BRIEF DESCRIPTION OF THE DRAWINGS

FIG. 1A: Raji-cells only, FIG. 1B: Raji-cells and NK cells at a ratio of 1:1, FIG. 1C: Raji-cells and NK-cells 1:10.

FIG. 2A: Raji-cells only, FIG. 2B: Raji-cells and NK cells at a ratio of 1:1, FIG. 2C: Raji-cells and NK cells at a ratio of 1:10.

FIG. 4A-C Percentages of viable lymphoma cells in the presence of NK cells as a function of the anti-CD20 antibody concentration. FIG. 4A: Raji-cells, FIG. 4B: SU-DHL4 cells, FIG. 4C: Z138 cells. NK cell to lymphoma cell ratio (E:T ratio) of 3:1.

FIG. 5A: Raji-cells, FIG. 5B: SU-DHL4 cells, FIG. 5C: Z138 cells. Anti-CD20 antibody concentration: 10 µg/ml.

EXAMPLE 1

Material and Methods

Cell Lines:

Raji-cells, SU-DHL4 cells and Z138 cell lines were obtained from ATCC (Manassas, Va., USA), from DSMZ (Braunschweig, Germany) and from Prof. M. Dyer (University of Leicester, UK), respectively. Raji-cells and SU-DHL4 cells were cultivated in RPMI 1640 medium (PAN Biotech, Cat. no. P04-18500) and Z138 in DMEM medium (PAN Biotech, Cat. no. P04-02500) supplemented with 10% FCS (Gibco, Cat. no. 10500-064) and Pen/Strep (Roche, Cat. no. 11 074 440 001) at 37° C. in a humidified incubator. Exponential growing cells with cell viability of 90% or more were used for the NK cell co-cultivation experiments.

Purification of NK Cells:

Whole blood was withdrawn from normal healthy donors into vaccutainer tubes (Becton Dickinson, Cat. no. 368484). PBMC were obtained by Ficoll preparation (PAN Biotech Cat. no. P04-60125). To leave the NK cells untouched, the NK cells were purified using a NK cell, negative selection kit (Miltenyi, Cat. no. 130-092-657). In short, the Ficoll isolated PBMCs were resuspended in MACS-buffer (PBS/0.5% BSA/2 mM EDTA) at $1 \times 10^7$ cells/40 µl. 10 µl of an NK-Cell-Biotin-Antibody cocktail was added to the cells and incubated for 10 min. at 4° C., followed by the addition of 30 µl MACS buffer. Thereafter, 20 µl of the NK-Cell-Microbead cocktail was added to the cells and incubated for 15 min. at 4° C. 2 ml of MACS-buffer was added and the cells were centrifuged for 10 min. at 300 g. The pellet was resuspended in 500 µl MACS-buffer and loaded onto the separation column which was equilibrated with 500 µl MACS-buffer before. The column was washed subsequently three times with 500 µl MACS-buffer and the cell number was determined in the total eluate using the CASY Cell Counter (Scharfe System).

The purity of the NK cell preparation was determined by staining of an aliquot of the MACS eluate. In short about $2 \times 10^5$ cells were resuspended in 100 µl RPMI 1640/10% FCS and stained with 10 µl each of anti-CD56-PE and anti-CD3-FITC antibodies (Becton Dickinson, Cat. no. 555516 and 555339, respectively) for 15 min at 4° C. Thereafter, 2 ml of RPMI 1640/10% FCS were added to the cells which were centrifuged for 5 min. at 400 g. The pellet was resuspended in 0.5 ml RPMI 1640/10% FCS and the percentage of the CD56 positive but CD3 negative cell fraction within the lymphocyte scatter gate was analyzed using a FACS Scan or FACS Canto II instrument (Becton Dickinson).

Purification of Monocytes:

Whole blood was withdrawn from normal healthy donors into vaccutainer tubes (Becton Dickinson, Cat. no. 368484). PBMC were obtained by Ficoll preparation (PAN Biotech Cat. no. P04-60125). To leave the monocytes untouched, the monocytes were purified using a negative selection, monocyte enrichment kit (Stem Cell Technologies, Cat No.: 19059).

CMFDA Staining of Lymphoma Cells:

The CMFDA lyophilizate (Invitrogen Cat. no. C7025) was resuspended in DMSO to obtain a 10 mM stock solution. $1 \times 10^6$ lymphoma cells were incubated for 30 min. at 37° C. in 1 ml complete medium supplemented with 1 µM CMFDA. Thereafter, cells were pelleted, washed once in complete medium and resuspended finally in complete medium at $1\times10^6$ cells/ml.

EXAMPLE 2

Generation of 3D Spheroids/Aggregates from Lymphoma Cell Lines

The lymphoma cell number was determined using a CASY instrument (Scharfe-Systems, Reutlingen) and the cell suspension was diluted in ice cold medium to $2.5\times10^4$ cells/ml (for 5,000 cells per spheroid/aggregate) and $5\times10^4$ cells/ml (for 10,000 cells per spheroid/aggregate). A volume of 200 µl of the cell suspension was added to each well of a 96-well plate with round (Corning Inc., New York, USA) or conical (Nunc, Roskilde, The Netherlands) bottom. To prevent cell attachment the plates were pre-coated with 50 µl 0.5% polyHEMA (Polysciences, Eppelheim, Germany) in 95% ethanol (v/v) and air dried at 37° C. for three days. The spheroid formation was initiated by centrifugation of the plates at 1,000 g for 10 min. using an Eppendorf 5810 centrifuge (Eppendorf AG, Hamburg, Germany) with swinging buckets. The plates were incubated under standard cell culture conditions at 37° C. and 7% $CO_2$ in humidified incubators.

EXAMPLE 3

Generation of 3D Spheroids/Aggregates from Solid Tumor Cell Lines

Monolayer cells were detached with Accutase (PAA Laboratories GmbH, Innsbruck, Austria) to generate a single cell suspension. The cell number was determined using a CASY instrument (Schärfe-Systems, Reutlingen) and the cell suspension was diluted in ice cold medium to $2.5\times10^4$ cells/ml (for 5,000 cells per spheroid/aggregate) and $5\times10^4$ cells/ml (for 10,000 cells per spheroid/aggregate). The rBM was thawed on ice overnight and added at a final concentration of 2.5% (v/v) with ice cold pipette tips to the cell suspension. A volume of 200 µl of the cell suspension was added to each well of a 96-well plate with round (Corning Inc., New York, USA) or conical (Nunc, Roskilde, The Netherlands) bottom. To prevent cell attachment the plates were pre-coated with 50 µl 0.5% polyHEMA (Polysciences, Eppelheim, Germany) in 95% ethanol and air dried at 37° C. for three days. The spheroid formation was initiated by centrifugation of the plates at 1,000 g for 10 min. using an Eppendorf 5810 centrifuge (Eppendorf AG, Hamburg, Germany) with swinging buckets. The plates were incubated under standard cell culture conditions at 37° C. and 7% $CO_2$ in humidified incubators.

EXAMPLE 4

Spheroid/Aggregate Lymphoma/NK Co-Cultivation and Incubation with Antibody

Figure 7:
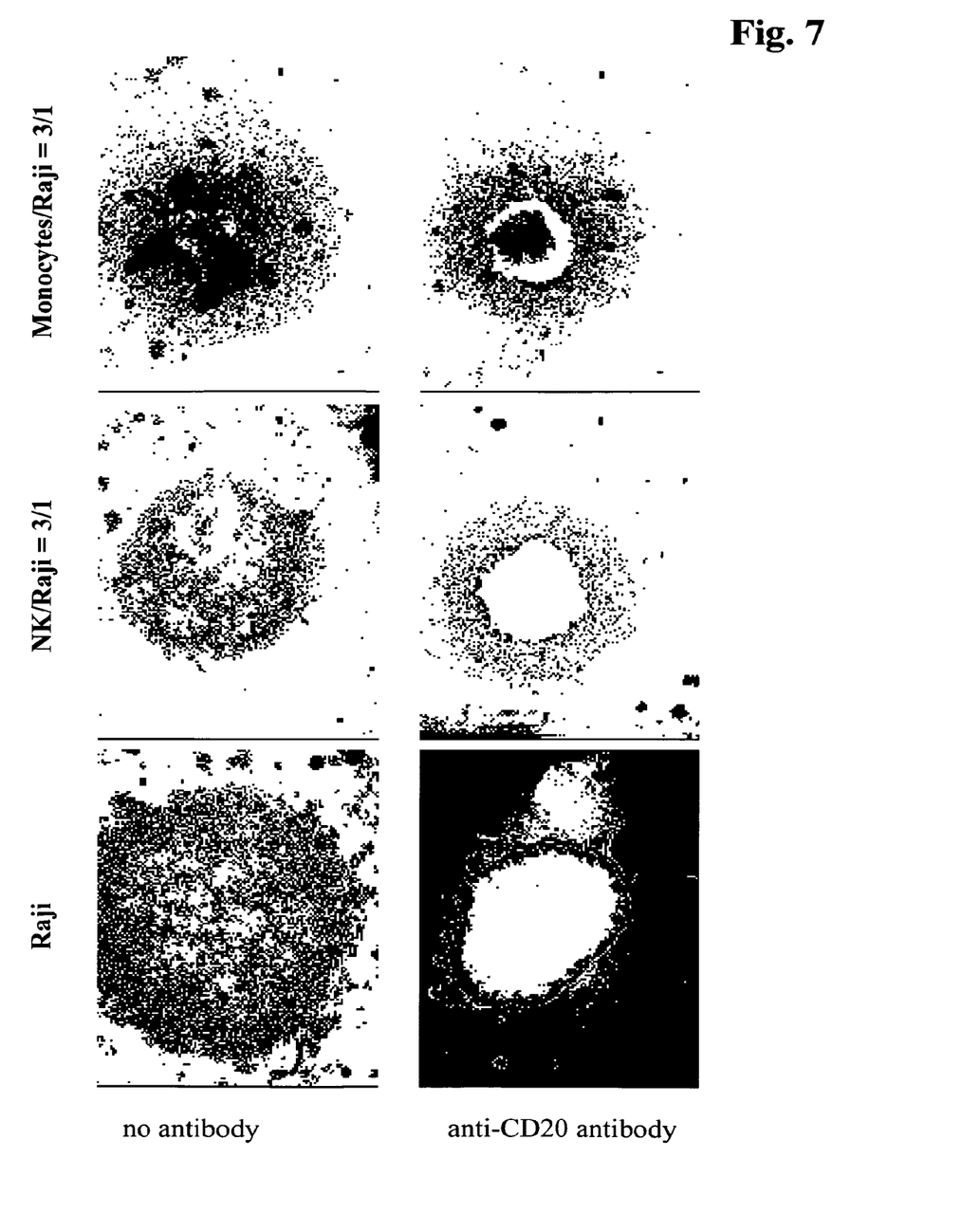
FIG. 7 Microscopic images of Raji-cells only and Raji cell co-cultivated with purified NK cells.

The sequence of cell co-cultivation and antibody addition can be varied. In an exemplary co-cultivation experiment, lymphoma cells (CMFDA labeled) and NK cells were mixed at ratios as indicated in 6 well plates. For example, an E:T (NK cell to lymphoma cell) ratio of 3:1 corresponds to a cell mixture of 3+1 (e. g. 75% NK cells and 25% lymphoma cells). 200 µl of the cell suspension was added to a single well of a polyHEMA coated 96 well V-plate (Nunc, Cat. no. 249662). PolyHEMA coating: 50 µl 0.5% polyHEMA in 95% ethanol per well; drying for 72 h at 37° C. (Polysciences, Cat. No. 18894). The plates were centrifuged for 10 min. at 1,000 g. The antibodies were added thereafter at concentrations as indicated above, and cell aggregates/spheroids were incubated at 37° C., 7% $CO_2$ in a humidified incubator. Microscopic images of Raji-cells only and Raji cell co-cultivated with purified NK cells are shown in FIG. 7, as well as images of co-cultivated Raji and monocyte cells to illustrate 3D co-cultivation of tumor cells with other immune cells then NK cells.

EXAMPLE 5

Viable Cell and Cell Death Analysis

Spheroids/aggregates were generated using 10,000 cells and incubated with the antibody as outlined in Examples 2 and 3. The identification of viable lymphoma tumor cells was as follows: Individual aggregates from individual wells representing identical experimental conditions were pooled, dissociated by pipetting and centrifuged at 300 g for 10 min. Individual spheroids were pooled, washed once with phosphate buffered saline (PBS), resuspended in Accutase solution, and incubated at 37° C. Every five minutes, the spheroids/aggregates were resuspended by pipetting and dissociation was complete within 5 to 15 min. Cells were washed using complete medium, centrifuged and cell pellets were resuspended in complete medium and propidium iodide was added at a concentration of 1 µg/ml (Sigma, Cat. no. P4170). Fluorescence analysis was performed by FACS analysis (Becton Dickinson, Canto II instrument).

Viable lymphoma cells were identified as shown in FIG. 1b. The upper right quadrant of PI and CMFDA positive cells represent the dead lymphoma cells, and the lower right quadrant of PI negative but CMFDA positive cells represent the viable lymphoma tumor target cell fraction. In the lower left quadrant are viable NK cells, whereas dead NK cells are located in the upper left quadrant.

In an alternative setting an apoptosis assay can be performed. Spheroids/aggregates were generated using 10,000 cells and incubated with the antibody as outlined in Examples 2 and 3. For apoptosis analysis, the spheroids/aggregates were transferred into a 96-well conical-bottom plate, washed once with phosphate buffered saline (PBS), resuspended in Accutase solution, and incubated at 37° C. Every five minutes, the spheroids/aggregates were resuspended by pipetting and dissociation was complete within 5 to 15 min. The single cell suspensions from eight spheroids/aggregates were pooled and cells were stained with annexin-V-fluos and propidium iodide in the presence of supplemented 2 mM $CaCl_2$, (annexin-V-fluos staining kit, Roche Diagnostics GmbH, Mannheim, Germany). The fluorescence of 10,000 cells was acquired using a flow cytometer (FACS scan instrument, Becton Dickinson, San Jose, Calif., USA). Quadrant statistics was applied on the dot plots, with the number of viable cells located in the lower-left quadrant.

To obtain the absolute number of dead and viable cells, the number of total cells from the spheroids/aggregates were counted using a Fuchs-Rosenthal cell counting chamber and multiplied with the percentage of viable or dead cells of the same spheroids/aggregates as determined from the annexin-V-fluos/PI staining.

The invention claimed is:
1. A method for the in vitro detection of effector function of an antibody, the method comprising the following steps:
   a) mixing natural killer cells and tumor cells, wherein the tumor cells are labeled with a first fluorescent dye capable of indicating the viability of the tumor cells, b) adding about $10^4$ mixed natural killer cells and tumor cells per 200 µl cell suspension to each of the wells of a multi-well plate, c) centrifuging the multi-well plate to induce the formation of a three-dimensional spheroid or a three-dimensional aggregate, d) adding the antibody at a concentration of 0.1 µg/ml to 15 µg/ml to the wells of the multi-well plate, e) incubating the multi-well plate for about 20 hours to about 72 hours, f) labeling dead cells in the wells with a second fluorescent dye, g) resuspending the spheroid or aggregate into individual cells and analyzing the percentage of viable cells in the wells of the multi-well plate by fluorescence activated cell sorting, and h) detecting the effector function of the antibody, wherein the detection of the effector function is percentage of viable cells and the effector function is antibody-dependent cellular cytotoxicity.

2. The method according to claim 1, wherein the natural killer cells are human natural killer cells.

3. The method according to claim 1, wherein the ratio of natural killer cells to tumor cells is from 10:1 to 1:10, from 1:2 to 1:4, or from 3:1 to 4:1.

4. The method according to claim 1, wherein the incubating is for about 20 hours to about 28 hours.

5. The method according to claim 1, wherein the centrifuging is for 10 minutes at 100 to 1,000 rpm.

6. The method according to claim 1, wherein the tumor cell is a lymphoma cell.

7. The method according to claim 6, wherein the lymphoma cell is selected from the group consisting of a Raji-cell, a SU-DHL4 cell, and a Z138 cell.

8. The method according to claim 1, wherein the antibody is added at a concentration of from 8 µg/ml to 12 µg/ml.

* * * * *